(12) United States Patent
Yribarren et al.

(10) Patent No.: US 7,927,305 B2
(45) Date of Patent: Apr. 19, 2011

(54) SYSTEMS, METHODS, AND DEVICES FOR INJECTING MEDIA CONTRAST

(75) Inventors: Travis Yribarren, Coarsegold, CA (US); Richard Newhauser, Redwood City, CA (US); Randolf von Oepen, Los Altos Hills, CA (US); James M. Jacobs, Mountain View, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/738,372

(22) Filed: Apr. 20, 2007

(65) Prior Publication Data

US 2007/0293821 A1    Dec. 20, 2007

Related U.S. Application Data

(60) Provisional application No. 60/793,781, filed on Apr. 21, 2006.

(51) Int. Cl.
*A61M 37/00* (2006.01)
*A61M 5/00* (2006.01)

(52) U.S. Cl. ........................................ 604/131; 600/432

(58) Field of Classification Search .................. 604/131, 604/151, 140, 141, 143; 600/431–434
See application file for complete search history.

(56) References Cited

U.S. PATENT DOCUMENTS

| | | |
|---|---|---|
| 4,624,381 A | 11/1986 | Freidrich |
| 4,832,681 A | 5/1989 | Lenck |
| 4,921,479 A | 5/1990 | Grayzel |
| 5,057,092 A | 10/1991 | Webster, Jr. |
| 5,180,366 A * | 1/1993 | Woods ........................ 604/96.01 |
| 5,195,978 A | 3/1993 | Schiffer |
| 5,250,069 A | 10/1993 | Nobuyoshi et al. |
| 5,320,605 A | 6/1994 | Sahota |
| 5,324,255 A | 6/1994 | Passafaro et al. |
| 5,378,237 A | 1/1995 | Boussignac et al. |
| 5,380,273 A | 1/1995 | Dubrul et al. |
| 5,385,563 A | 1/1995 | Gross |
| 5,405,380 A | 4/1995 | Gianotti et al. |
| 5,423,773 A | 6/1995 | Jimenez |
| 5,437,288 A | 8/1995 | Schwartz et al. |

(Continued)

FOREIGN PATENT DOCUMENTS

EP    0 279 959    8/1988

(Continued)

OTHER PUBLICATIONS

U.S. Appl. No. 11/738,384, filed Apr. 20, 2007, Von Oepen.

(Continued)

*Primary Examiner* — Nicholas D Lucchesi
*Assistant Examiner* — Michael J Anderson
(74) *Attorney, Agent, or Firm* — Workman Nydegger

(57) ABSTRACT

A system for delivering a contrast medium to a treatment site including a delivery device, and a portable power injector. The delivery device includes a guidewire lumen and a contrast injection lumen, the guidewire lumen and contrast injection lumen being at least partially coaxial. The portable power injector includes an injector body and is configured to contain a contrast medium. The injector body has a plunger disposed therein. The portable power injector also includes a pressure generator, the pressure generator being configured to apply a pressure to the plunger to drive the contrast medium from the injector body and through a distal end of the contrast injection lumen.

6 Claims, 4 Drawing Sheets

U.S. PATENT DOCUMENTS

| | | | |
|---|---|---|---|
| 5,443,454 A | 8/1995 | Tanade et al. | |
| 5,454,795 A | 10/1995 | Samson | |
| 5,460,608 A | 10/1995 | Lodin et al. | |
| 5,507,751 A | 4/1996 | Goode et al. | |
| 5,647,846 A | 7/1997 | Berg et al. | |
| 5,662,622 A | 9/1997 | Gore et al. | |
| 5,702,439 A | 12/1997 | Keith et al. | |
| 5,709,658 A | 1/1998 | Sirhan et al. | |
| 5,720,735 A | 2/1998 | Dorros | |
| 5,855,563 A | 1/1999 | Kaplan et al. | |
| 5,906,606 A | 5/1999 | Chee et al. | |
| 5,951,517 A * | 9/1999 | Lampropoulos et al. | 604/151 |
| 6,017,324 A | 1/2000 | Tu et al. | |
| 6,022,309 A | 2/2000 | Celliers et al. | |
| 6,152,909 A | 11/2000 | Bagaoisan et al. | |
| 6,210,393 B1 | 4/2001 | Brisken | |
| 6,210,404 B1 | 4/2001 | Shadduck | |
| 6,217,503 B1 | 4/2001 | Weinberger et al. | |
| 6,261,273 B1 | 7/2001 | Ruiz | |
| 6,299,595 B1 | 10/2001 | Dutta et al. | |
| 6,327,505 B1 | 12/2001 | Medhkour et al. | |
| 6,398,772 B1 | 6/2002 | Bond et al. | |
| 6,398,791 B1 | 6/2002 | Que et al. | |
| 6,416,740 B1 | 7/2002 | Unger | |
| 6,440,161 B1 | 8/2002 | Madrid et al. | |
| 6,461,383 B1 | 10/2002 | Gesswein et al. | |
| 6,482,218 B1 | 11/2002 | Tran | |
| 6,579,246 B2 | 6/2003 | Jacobsen et al. | |
| 6,582,390 B1 | 6/2003 | Sanderson | |
| 6,652,508 B2 | 11/2003 | Griffin et al. | |
| 6,679,879 B2 | 1/2004 | Shadduck | |
| 6,682,502 B2 | 1/2004 | Bond et al. | |
| 6,790,170 B2 | 9/2004 | Moody et al. | |
| 6,849,077 B2 | 2/2005 | Ricci | |
| 6,869,416 B2 | 3/2005 | Windheuser et al. | |
| 6,942,680 B2 | 9/2005 | Grayzel et al. | |
| 7,044,933 B2 * | 5/2006 | VanDiver et al. | 604/151 |
| 7,329,223 B1 * | 2/2008 | Ainsworth et al. | 600/300 |
| 2001/0008976 A1 | 7/2001 | Wang | |
| 2001/0031243 A1 | 10/2001 | Unger | |
| 2002/0022831 A1 | 2/2002 | O'Connor et al. | |
| 2002/0072710 A1 | 6/2002 | Stewart et al. | |
| 2002/0107473 A1 | 8/2002 | Bond et al. | |
| 2002/0123716 A1 | 9/2002 | VanDiver et al. | |
| 2002/0123738 A1 | 9/2002 | Jansen et al. | |
| 2003/0009157 A1 | 1/2003 | Levine et al. | |
| 2003/0055377 A1 | 3/2003 | Sirhan et al. | |
| 2003/0069522 A1 | 4/2003 | Jacobsen et al. | |
| 2003/0135261 A1 | 7/2003 | Kugler et al. | |
| 2003/0191449 A1 * | 10/2003 | Nash et al. | 604/523 |
| 2004/0044350 A1 | 3/2004 | Martin et al. | |
| 2004/0054322 A1 | 3/2004 | Vargas | |
| 2004/0054347 A1 | 3/2004 | Zadno-Azizi et al. | |
| 2004/0093044 A1 | 5/2004 | Rychnovsky et al. | |
| 2004/0098021 A1 | 5/2004 | Laguna | |
| 2004/0102821 A1 | 5/2004 | Kawata et al. | |
| 2004/0103516 A1 | 6/2004 | Bolduc et al. | |
| 2004/0220473 A1 | 11/2004 | Lualdi | |
| 2004/0225278 A1 | 11/2004 | Poole et al. | |
| 2004/0230204 A1 | 11/2004 | Wortley et al. | |
| 2005/0004522 A1 | 1/2005 | Katoh et al. | |
| 2005/0021004 A1 | 1/2005 | Cully et al. | |
| 2005/0182371 A1 | 8/2005 | Wagner et al. | |
| 2005/0209582 A1 | 9/2005 | Quinn et al. | |
| 2006/0085023 A1 | 4/2006 | Davies, Jr. et al. | |
| 2006/0190022 A1 * | 8/2006 | Beyar et al. | 606/192 |
| 2007/0060880 A1 | 3/2007 | Gregorich et al. | |
| 2007/0250149 A1 | 10/2007 | Von Oepen | |
| 2007/0299392 A1 * | 12/2007 | Beyar et al. | 604/96.01 |

FOREIGN PATENT DOCUMENTS

| | | |
|---|---|---|
| EP | 0 596 635 | 5/1994 |
| EP | 0 598 635 | 5/1994 |
| EP | 0 916 359 | 5/1999 |
| EP | 1 475 120 | 11/2004 |
| EP | 1 607 119 | 12/2005 |
| GB | 2 143 920 | 2/1985 |
| WO | WO 88/08727 | 11/1988 |
| WO | WO 93/06780 | 4/1993 |
| WO | WO 96/07448 | 3/1996 |
| WO | WO 96/39205 | 12/1996 |
| WO | WO 97/23158 | 7/1997 |
| WO | WO 97/39690 | 10/1997 |
| WO | WO 99/15070 | 4/1999 |
| WO | WO 99/17826 | 4/1999 |
| WO | WO 99/21600 | 5/1999 |
| WO | WO 99/64098 | 12/1999 |
| WO | WO 00/03756 | 1/2000 |
| WO | WO 01/03762 | 1/2001 |
| WO | WO 01/07101 | 2/2001 |
| WO | WO 03/057060 | 7/2003 |
| WO | WO 03/105671 | 12/2003 |
| WO | WO 2004/064891 | 8/2004 |
| WO | WO 2004/096338 | 11/2004 |
| WO | WO 2006/002199 | 1/2006 |
| WO | WO 2006/058434 | 6/2006 |
| WO | WO 2006/122243 | 11/2006 |

OTHER PUBLICATIONS

U.S. Appl. No. 11/738,382, filed Apr. 20, 2007, Von Oepen.
U.S. Appl. No. 11/738,378, filed Apr. 20, 2007, Von Oepen.
U.S. Appl. No. 11/738,368, filed Apr. 20, 2007, Jacobs.
U.S. Appl. No. 11/738,386, filed Apr. 20, 2007, Von Oepen.
PCT/US07/67244, Apr. 23, 2007, PCT.
PCT/US07/67237, Apr. 23, 2007, PCT.
PCT/US07/67238, Apr. 23, 2007, PCT.
PCT/US07/67239, Apr. 23, 2007, PCT.
PCT/US07/67240, Apr. 23, 2007, PCT.
PCT/US07/67242, Apr. 23, 2007, PCT.
PCT/US07/67243, Apr. 23, 2007, PCT.
U.S. Appl. No. 60/793,781, filed Apr. 21, 2006, Von Oepen.
U.S. Appl. No. 11/738,382, mail date Jan. 4, 2008, Office Action.
U.S. Appl. No. 11/738,382, mail date Aug. 11, 2008, Office Action.
U.S. Appl. No. 11/738,382, mail date Feb. 20, 2009, Office Action.
U.S. Appl. No. 11/738,382, mail date Aug. 20, 2009, Office Action.
U.S. Appl. No. 11/738,368, mail date Jan. 23, 2008, Office Action.
U.S. Appl. No. 11/738,368, mail date Sep. 16, 2008, Office Action.
U.S. Appl. No. 11/738,368, mail date Jan. 27, 2009, Office Action.
U.S. Appl. No. 11/738,378, mail date Sep. 2, 2009, Office Action.
U.S. Appl. No. 11/738,368, mail date Sep. 3, 2009, Office Action.
U.S. Appl. No. 11/738,386, mail date Sep. 28, 2009, Office Action.
U.S. Appl. No. 11/738,386, mail date Apr. 22, 2010, Office Action.
U.S. Appl. No. 11/738,378, mail date May 12, 2010, Office Action.
U.S. Appl. No. 11/738,382, mail date Apr. 20, 2010, Office Action.
U.S. Appl. No. 11/738,384, mail date Mar. 2, 2010, Office Action.
U.S. Appl. No. 11/738,384, mail date May 24, 2010, Office Action.
U.S. Appl. No. 11/738,384, mail date Oct. 27, 2010, Office Action.
U.S. Appl. No. 11/738,378, Oct. 4, 2010, Advisory Action.
U.S. Appl. No. 11/738,378, mail date Aug. 17, 2010, Office Action.

* cited by examiner

SYSTEMS, METHODS, AND DEVICES FOR INJECTING MEDIA CONTRAST

CROSS-REFERENCE TO RELATED APPLICATIONS

This application claims the benefit of the U.S. Provisional Patent Application No. 60/793,781, filed Apr. 21, 2006, and entitled "Medical Devices," which is incorporated herein by reference in its entirety.

BACKGROUND

1. Technical Field

The present disclosure relates to systems, devices, and methods for delivering a contrast medium to a treatment site within a blood vessel.

2. Related Art

Cardiovascular disease is a leading cause of death worldwide. Consequently, many efforts have been directed at treating cardiovascular disease. During vascular intervention procedures, guidewires or other instruments are often utilized. In order to view the relative position of the instruments during a procedure, radiopaque contrast dye is frequently used to visualize the vascular system via x-ray.

The contrast medium is generally injected through a guiding catheter using a syringe or power injector. In some cases, a relatively high volume of contrast media is required over the entire procedure, such as during the treatment of chronic total occlusions (CTOs), since the procedure can require extensive time and lesion visualization. This can cause harm to the patient's kidneys, and is therefore undesirable. In addition, contrast injections using a syringe can be quite difficult, high enough pressure to inject the highly viscous contrast media.

Some approaches for generating these pressures include manually generating the pressure, such as with a syringe, or using a large piece of equipment known as a "power injector." Manually generating the pressure for the highly viscous fluid over the course of a procedure may become overly burdensome. Power injectors frequently include a pump and a reservoir as part of a powered, stationary system. Such systems are often bulky, expensive, and injection high volumes of contrast.

In addition, some approaches require that contrast medium be injected at two separate locations within the vascular system. For example, during the treatment of a chronic total occlusion (CTO), it may be desirable to visualize the proximal and distal cap of the CTO, perhaps even simultaneously. In this case, due to the significant expense of power injectors, it is unlikely that there would be two power injectors in the operation room. Therefore, a second contrast injection system would be useful, and this invention offers an effective and inexpensive option for such a situation.

SUMMARY

According to one example, a system for delivering a contrast medium to a treatment site includes a delivery device and a portable power injector. The delivery device includes a guidewire lumen and a contrast injection lumen, the guidewire lumen and contrast injection lumen being at least partially coaxial. The portable power injector includes a pneumatically actuated injector body and is configured to contain a contrast medium. The injector body has a plunger disposed therein. The portable power injector also includes a pressure generator, the pressure generator being configured to apply a pressure to the plunger to drive the contrast medium from the injector body and through a distal end of the contrast injection lumen.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above recited and other advantages and features can be obtained, a more particular description of the subject matter briefly described above will be rendered by reference to specific embodiments, which are illustrated in the appended drawings. Understanding that these drawings depict only typical embodiments and are not, therefore, to be considered to be limiting in scope, embodiments will be described and explained with additional specificity and detail through the use of the accompanying drawings in which.

DETAILED DESCRIPTION

Systems, devices, and methods are provided herein for delivering a contrast medium in a controlled manner to the vasculature of a patient. In one example, a system includes a portable power injector coupled to a delivery device. The delivery device may be configured to simultaneously provide support for a guidewire or other instrument and deliver a contrast medium at a location near the treatment site. Delivering the contrast medium near the treatment site may reduce the amount of contrast medium used in visualizing the test site during a vascular intervention procedure.

In particular, delivering the contrast medium near the treatment site may reduce the amount of contrast medium used in visualizing the treatment site as the contrast medium may be delivered to a relatively confined location near the treatment site rather than filling a larger region leading up to the treatment site. The delivery device may also include an expandable member that expands as the contrast medium is applied. As the expandable member expands, it restricts the flow of contrast medium, thereby retaining contrast medium near the treatment site, which may reduce the amount of contrast used to provide visualization of the treatment site.

The portable power injector may include a portable pressure generator coupled to a injector body. A contrast medium may be stored in the injector body. The portable pressure generator applies pressure to a plunger in the injector body to selectively drive the contrast medium to the delivery device. The portable pressure generator may also include an actuation control to allow a practitioner to control the delivery of the contrast medium. Such a configuration may allow the practitioner to readily control the flow of contrast medium to the delivery device, which may allow for a reduction in the amount of contrast medium used in visualizing the treatment site during a vascular intervention procedure.

It should be apparent from the following description that the delivery device and portable power injector are capable of functioning independently or in combination, in accordance with this invention. For example, the portable power injector may be used to deliver a contrast agent through a guide catheter to the site of an obstruction, without the need for the delivery device.

The accompanying drawings illustrate various embodiments of the present system and method and are a part of the specification. The illustrated embodiments are merely examples of the present system and method and do not limit the scope of the disclosure. Throughout the drawings, identical reference numbers designate similar, but not necessarily identical, elements.

Figure 1:
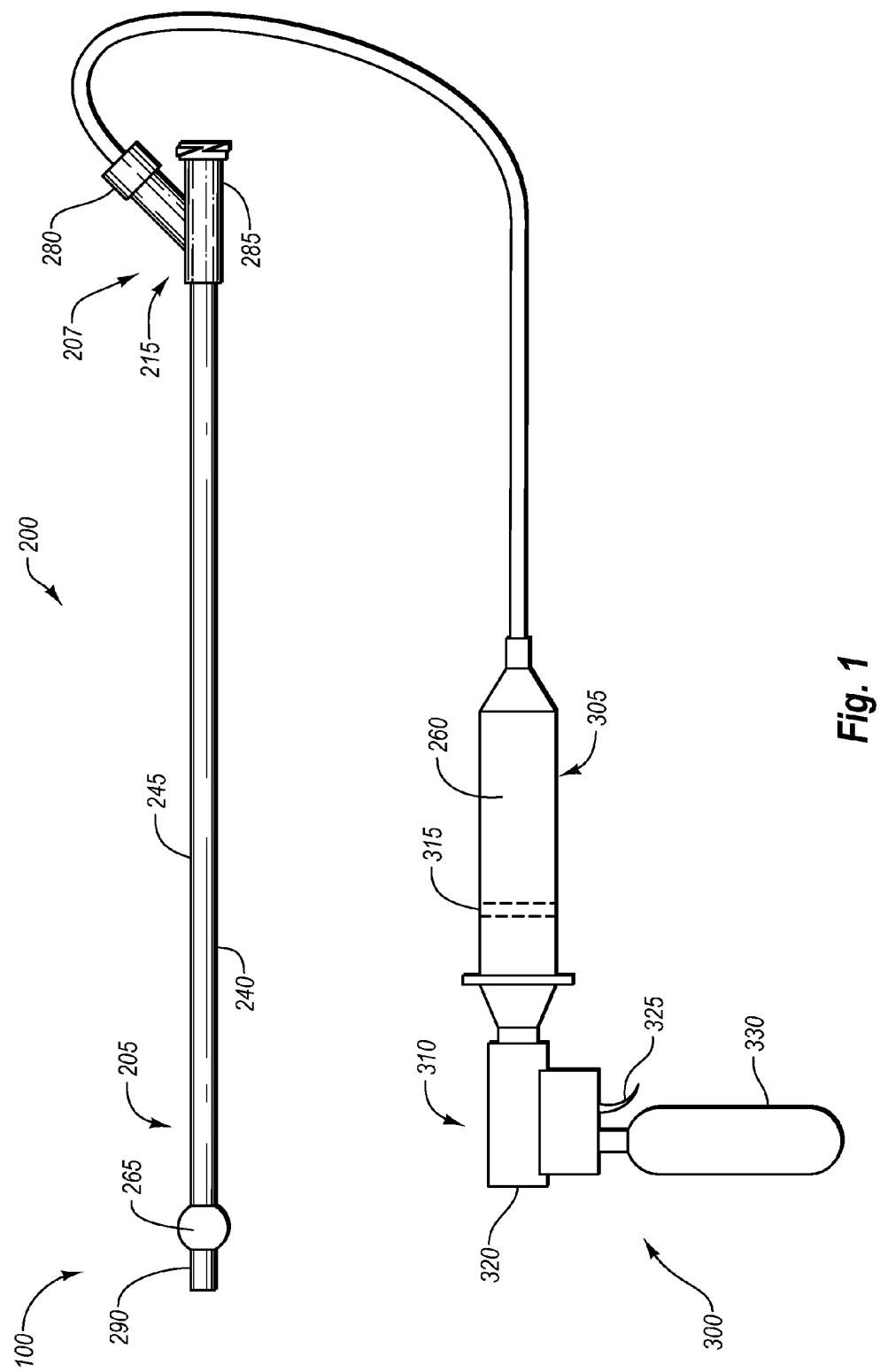
FIG. 1 illustrates a system for delivering contrast medium according to one example.

FIG. 1 illustrates a system 100 configured to deliver a contrast medium to a treatment site. The system 100 includes a delivery device 200 coupled to a portable power injector device 300. The delivery device 200 provides a tubular structure through which a contrast medium can be delivered from the portable power injector device 300. In particular, a distal end 205 of the delivery device 200 may be positioned near a treatment site. The delivery device 200 is configured to provide access through the distal end 205 for an instrument, such as a guidewire or other instrument, allowing the instrument to cross an obstruction at the treatment site as part of a vascular intervention procedure. During the procedure, it may be desirable to deliver a contrast medium to the treatment site. In one example, the portable power injector 300 may be used to inject the contrast medium through the delivery device 200 and out the distal end of the delivery device 205. The delivery device 200 is the conduit directing the contrast medium to the treatment site.

As will be discussed in more detail below, the delivery device 200 may be configured to increase the dwell time of the contrast medium near the treatment site while reducing the amount of contrast medium used in providing visualization. In addition, the portable power injector device 300 is a portable device that may be configured to deliver a contrast medium in a variety of settings. One example of delivery of a contrast medium through the delivery device 200 will be discussed in more detail with reference to FIGS. 2A-2F and 3.

Figure 2A:
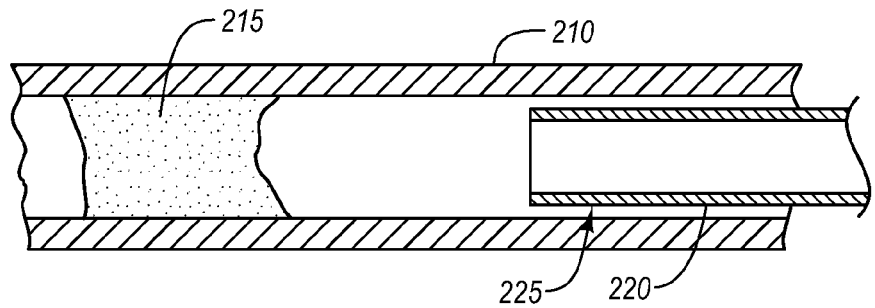
FIG. 2A is a cross-sectional view of a vessel having an obstruction therein in which a guide catheter is introduced according to one example.

FIG. 2A is a cross-sectional view of a vessel 210 having an obstruction 215 therein. As illustrated in FIG. 2A, a guide catheter 220 has been introduced according to one example. The guide catheter 220 may be introduced to the vessel 210 by way of a puncture or other proximal opening. A distal end 225 of the guide catheter 220 may then be advanced until it is near the obstruction 215.

Figure 2B:
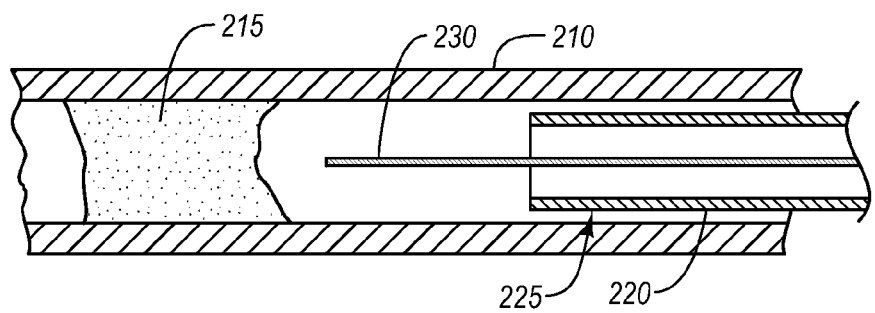
FIG. 2B is a cross-sectional view of a vessel in which a distal end of a guidewire is initially positioned relative to the obstruction according to one example.

As illustrated in FIG. 2B, a guidewire 230 is advanced through the guide catheter 220 until a distal end 235 of the guidewire 230 is initially positioned relative to the obstruction 215. It will be understood, that in some configurations, the guide catheter 220 can include a rotating hemostasis valve (RHV) to facilitate access and delivery of other medical devices and/or contrast media.

Figure 2C:
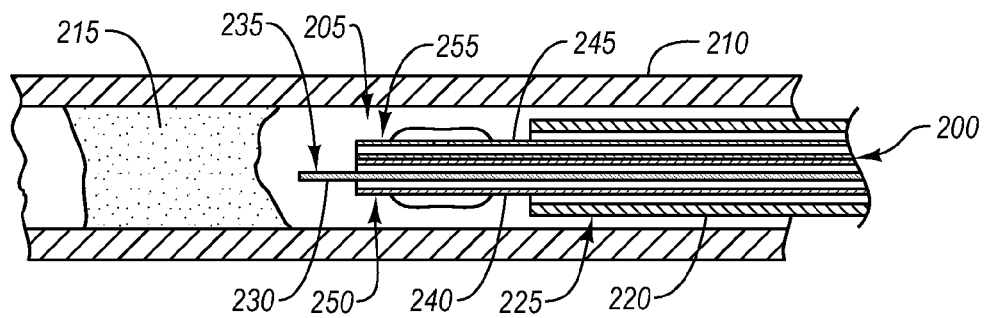
FIG. 2C is a cross-sectional view of a vessel in which a delivery device is tracked into position relative to the guidewire and the guide catheter according to one example.

Once the distal end 235 of the guide wire 230 is initially positioned relative to the obstruction 215, a distal end 205 of the delivery device 200 is tracked over the guidewire 230 into position relative to the obstruction 215, as illustrated in FIG. 2C. The delivery device 200 may be of any suitable type, such as a rapid exchange (RX) or over-the-wire (OTW) type catheter.

The delivery device 200 includes a plurality of lumens including a guidewire lumen 240 and a contrast injection lumen 245. The guidewire lumen 240 is sized to receive and provide support to the guidewire 230. The guidewire lumen 240 may track over the guidewire 230. As a result, the distal end 205 of the delivery device 200 may be positioned relative to the obstruction 215 by tracking the guidewire lumen 240 over the guidewire 230. In one example, the guidewire lumen 240 may be coaxial with the contrast injection lumen 245, however other non-coaxial or off-axis configurations are also possible.

As illustrated in FIG. 2C, the guidewire lumen 240 provides support for the guidewire 230. Generally, it is desirable for the delivery device 200 to provide adequate pushability to provide support to the guidewire 230 during passage of the guidewire 230 through the obstruction 215. To increase the stiffness and axial rigidity of the delivery device 200, an adhesive bead can be applied between the guidewire lumen 240 and the contrast injection lumen 245. By coupling the two lumens together, the axial rigidity is increased, the possibility of guidewire 230 or delivery device 200 buckling is reduced, and additional support is provided to the guidewire 230 during passage through the obstruction 215.

Increased axial rigidity can also be obtained through extruding both the guidewire lumen 240 and the contrast injection lumen 245 together such that the guidewire lumen 240 and the contrast injection lumen 245 are joined. Further, other approaches may also be used to stiffen the delivery device 200 and increase the pushability of the delivery device 200. Further, a distal end 250 of the guidewire lumen 240 may terminate distally to a distal end 255 of the contrast injection lumen 245. This configuration and orientation allows contrast medium to be injected proximal to the guidewire 230.

Figure 2D:
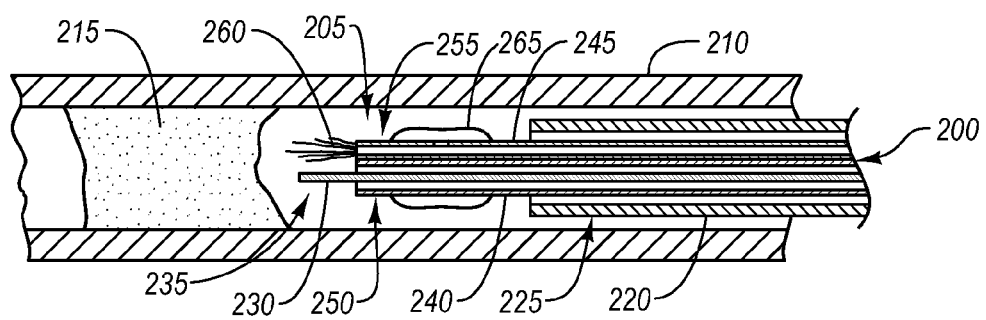
FIG. 2D is a detailed view of a distal end of a guidewire support according to one example in which contrast medium is being delivered according to one example.

FIG. 2D is a cross-sectional view of the vessel in which a contrast medium 260 is introduced through the distal end 205 of the delivery device 200 (FIG. 1). In addition, such a configuration may improve visualization of the treatment site near the obstruction 215. For example, the contrast medium 260 can be injected through the delivery device 200 to the treatment site, thereby providing additional visualization of the disease and the progress of the distal end 235 of the guidewire 230 as it crosses the obstruction 215.

Introducing the contrast medium 260 near the obstruction 215 may reduce the amount of contrast medium used to visualize the area around the obstruction 215. In particular, a volume of the contrast medium 260 sufficient for visualization may be roughly proportional to the distance between the position where the contrast medium 260 is introduced and the obstruction 215. This procedure positions the distal end 205 of the device 200 close to the obstruction 215 reducing the amount of contrast medium 260 used in the visualization of the area near the obstruction.

Figure 2E:
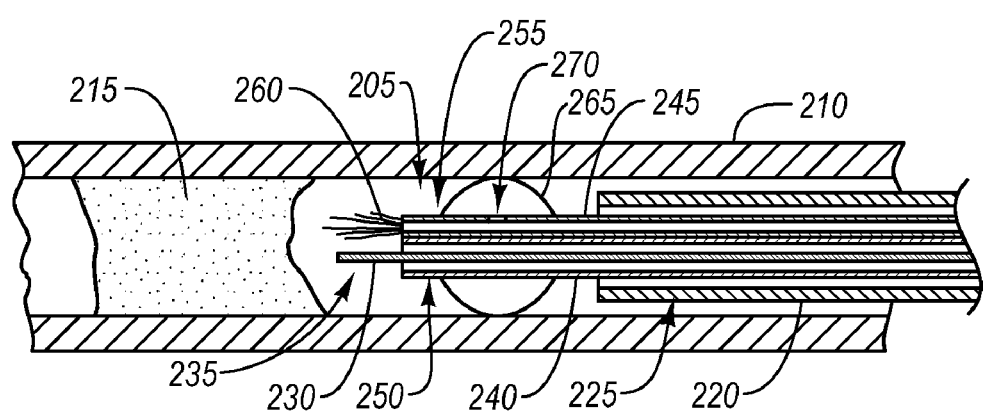
FIG. 2E is a detailed view of a distal end of a guidewire support in which an expandable member is expanding as a contrast medium is delivered according to one example.

Further, as illustrated in FIGS. 2D and 2E, the distal end 205 of the delivery device 200 may further include an expandable member 265, which may be selectively expanded as the contrast medium 260 is introduced. The expandable member 265 may be expanded to contain the contrast medium 260.

The expandable member 265 may be a balloon-type expandable member located near the distal end 205 of the delivery device 200. The expandable member 265 illustrated may be disposed circumferentially about the distal end 205. The expandable member 265 is placed in fluid communication with the contrast injection lumen 245. In particular, in one example, an opening such as a fluid port 270 fluidly couples the expandable member 265 and the contrast injection lumen 245.

Accordingly, as contrast medium 260 flows to the distal end 255 of the contrast injection lumen 245, a portion of the contrast medium 260 directed toward the distal end 255 will flow through the fluid port 270 and into the expandable member 265. As the contrast medium 260 flows into the expandable member 265, the expandable member 265 expands. As the expandable member 265 expands it restricts the flow of contrast medium 260 back from the obstruction 215, as illustrated in FIG. 2E.

The contrast medium 260 is thereby delivered into the vessel 210 and the expandable member 265 is simultaneously expanded, thereby occluding the treatment vessel proximal to the distal end 205 of the delivery device 200. Since the expandable member 265 is expanded simultaneously with injection of contrast medium 260 into the vessel 210, some amount of blood and contrast medium 260 will be forced proximal to the expandable member 265 before the vessel is occluded, and therefore, the treatment site region will predominantly contain contrast medium 260. Such a configuration may enhance the suitability of conditions near the obstruction for visualization under x-ray. Thus, visualization may be performed as desired while the contrast medium 260 is trapped at the treatment site.

When pressure in the contrast injection lumen 245 is removed, the expandable member 265 may deflate, thereby re-establishing flow within the vessel 210. This procedure can be repeated as desired. As introduced, visualization of the treatment site may allow for a practitioner to track the progress of the guidewire 240 or other instrument in crossing the obstruction 215.

Figure 2F:
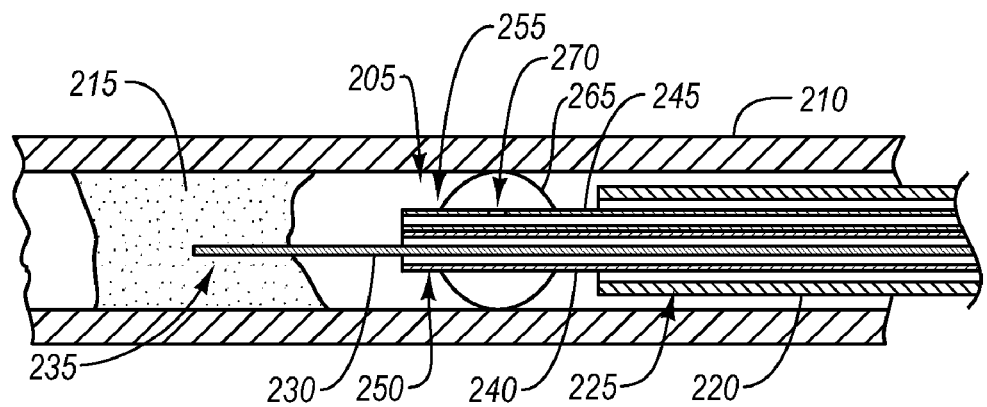
FIG. 2F is a cross-sectional view of a vessel with a guidewire crossing the obstruction according to one example.

The guidewire 230 crossing the obstruction 215 is illustrated in FIG. 2F. The above steps have been presented in one particular order. The order in which the steps are performed may be varied as desired and indeed one or more steps may be omitted as desired. Further, the steps above have been described with reference to the distal end 205 of the delivery device 200 without regard to how the guidewire 230 and contrast medium 260 are introduced to the guidewire lumen 240 and the contrast injection lumen 245 respectively. Any suitable configuration may be utilized to accomplish this.

As illustrated in FIG. 1, the proximal end 207 of the delivery device 200 may be coupled to a source for receiving the contrast medium 260 (FIG. 2D), such as the portable power injector 300. In particular, as illustrated in FIG. 1, the proximal end 207 of the delivery device 200 may include a fitting 215, such as a luer-type fitting or a rotating hemostatic valve (RHV) cooperating with another fitting.

The fitting 215 illustrated in FIG. 1 includes a contrast medium fitting 280 in communication with the contrast inject lumen 245 and a guidewire fitting 285 in communication with the guidewire lumen 240. In one example, the configuration of the guidewire fitting 285 allows for guidewire exchange. In particular, after tracking the delivery device 200 into place, one guidewire may be removed from the delivery device 200, and a new wire may be introduced to attempt crossing the obstruction 215 (FIG. 2A).

The materials and construction of the delivery device 200 may be varied to achieve the optimal combination of torque transmission and guidewire support. For example, the guidewire lumen 240 and/or the contrast injection lumen 245 may be formed from plastic, metal, other materials, or any combination thereof. Further, the delivery device 200 may include a construction that varies axially, as in the case of a rapid exchange catheter with a distal plastic construction and a proximal, metallic hypotube construction. Further, it may be desirable for the delivery device 200 to include a metallic tip 290 to aid in crossing the obstruction 215. In addition to a single guidewire lumen 240, other configurations are possible, such as multiple guidewire lumens.

As mentioned above, the method described above may also be carried out with a system that includes a rotating hemostatic valve (RHV) and associated guide catheter, which functions as a tubular structure, that cooperates with a guidewire and a portable power injector. The guide catheter and RHV combination would replace the delivery device 200 described herein, providing support to the guidewire, and permitting the transmission of a contrast media or agent from the portable power injector to the distal end of the guide catheter adjacent to the treatment site. When using a guide catheter, as known to those skilled in the art, additional contrast media or agent could be used. This can be an alternative system that may be useful as a secondary system during the treatment of a CTO, for example.

As introduced, the portable power injector 300 is illustrated as being coupled to the contrast injection lumen 245 by way of the contrast medium fitting 280. The portable power injector 300 illustrated in FIG. 1 includes an injector body 305 coupled to a portable pressure generator 310. The injector body 305 has fluid communication to the delivery device 200 and is also coupled to the pressure generator 310. The injector body 305 may be filled with contrast medium to be delivered to the delivery device 200. The injector body 305 can have various configurations to perform the identified function. For instance, the injector body can be cylindrical or have a generally circular cross-section. It will be understood, however, the injector body can have various other elongate and cross-sectional configurations. For instance, the injector body can be tapered or have a square, rectangular, oval, curved, polygonal, or other cross-sectional configuration.

The injector body 305 includes a plunger 315 disposed therein. The portable pressure generator 310 applies pressure to the plunger 315 to thereby force contrast medium 260 to the delivery device 200. The pressure generator 310 may make use of any pressure generating principles. For example, the pressure generator 310 may include a linear motor that is actuated to drive the plunger 315. A hydraulic system can be used to generate the pressure. A pneumatic system can be used to generate the pressure.

The pressure generator 310 may include an actuation control 320. The actuation control 320 may include mechanical or electrical mechanisms to control the duration that pressure is applied to the plunger 315, thereby controlling the amount of contrast medium 260 delivered through the delivery device 200. Such a configuration may offer greater control of the total injection volume, thus allowing a practitioner to utilize less contrast medium 260.

In the example illustrated in FIG. 1, the actuation control 320 includes a trigger mechanism 325. The trigger mechanism controls a valve mechanism connected to a compressed gas reservoir 330. When the actuation control 320 is actuated, compressed gas from the compressed gas reservoir 330 flows through the actuation control 320 to the injector body 305. When the compressed gas flows into the injector body 305, the compressed gas applies pressure to the plunger 315 thereby forcing the plunger 315 against the contrast medium 260. The contrast medium 260 is thereby expelled from the injector body 305 to the delivery device 200. In addition to providing contrast medium 260 within the injector body 305, an additional reservoir may be provided.

Figure 3:
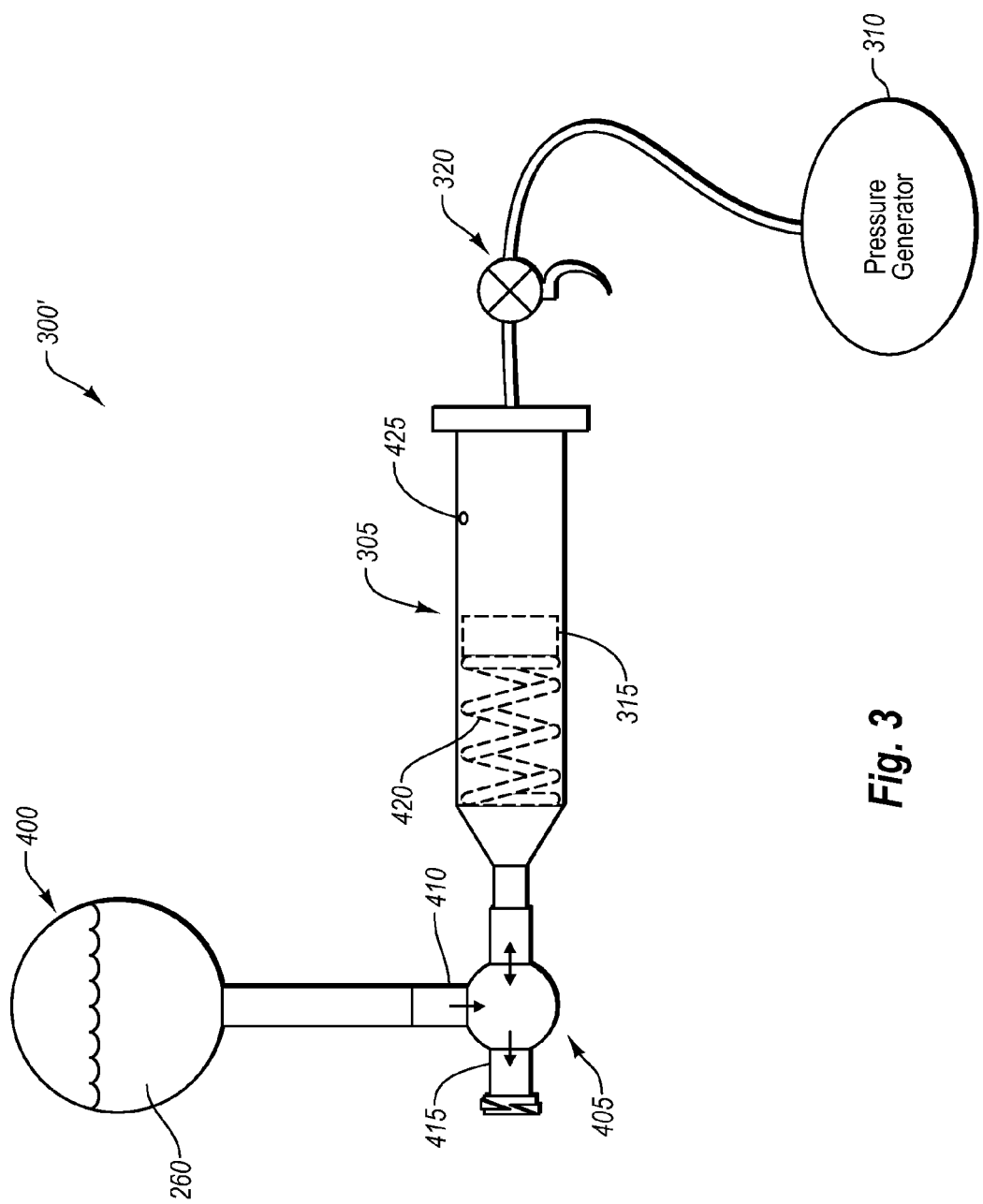
FIG. 3 illustrates a portable power injector according to one example.

FIG. 3 is a schematic diagram of a portable power injector 300', which includes a contrast medium reservoir 400. The portable power injector 300' includes a injector body 305 and a pressure generator 310. The injector body 305 may be configured to direct contrast medium 260 to the delivery device 200 (FIG. 1) as described above. In addition, the portable power injector 300' is configured to be refilled by the contrast medium reservoir 400. In particular, the contrast medium reservoir 400 may be used to refill the injector body 305.

The portable power injector 300' may include a connection configured to control the flow of control medium 260 from the contrast medium reservoir 400, as well as the flow of control medium between the injector body 305 and the delivery device 200 (FIG. 1). In particular, the portable power injector 300' may include a three-passage connection 405. The three-passage connection 405 includes a reservoir check valve 410 and a delivery check valve 415.

The reservoir check valve 405 allows liquid to flow from the passage associated with the contrast medium reservoir 400 while preventing the flow of liquid in the opposite direction. Accordingly, contrast medium 260 may be driven from the contrast medium reservoir 400 into the three-passage connection 405. In one example, the contrast medium 260 entering the three-passage connection 405 would be able flow toward either the delivery device 200 (FIG. 1) or toward the injector body 305.

The portable power injector 300' may be configured to allow a user to establish a relatively low pressure within the injector body 305 to cause the contrast medium 260 to be directed to the injector body 305. This low pressure may be established by proximal movement of the plunger 315. Alternatively, the pressure generator 310 may be configured to allow the user to establish a relatively low pressure in the injector body 305 such that the contrast medium 260 from the contrast medium reservoir 400 is drawn into the injector body 305. Accordingly, the contrast medium reservoir 400 may be configured to refill the injector body 305.

As introduced, the portable power injector 300 illustrated in FIG. 3 is configured to allow a user to establish low pressure within the injector body 305 for refilling the injector body 305. The delivery check valve 415 is configured to reduce or eliminate the flow of contrast medium or other liquids from the delivery device 200 (FIG. 1) back into the portable power injector 300'.

In particular, delivery check valve 415 is configured to allow liquid to flow out of the portable power injector 300 while preventing liquid from flowing the opposite direction. Accordingly, when low pressure is established in the injector body 305, the delivery check valve 415 closes. Similarly, when the plunger 315 is urged distally, the delivery check valve 415 opens to allow contrast medium 260 to flow to the delivery device 200 (FIG. 2).

FIG. 3 also illustrates a biasing member 420, such as a spring, placed within the injector body 305. The biasing member 420 may be configured to act upon the plunger 315 to bias the plunger 315 in the proximal direction. This bias may be in direct opposition to the pressure applied by the pressure generator 310 to the plunger in the distal direction.

A pressure release feature 425 may also be included in the portable power injector 300' proximal to the plunger 315, thereby allowing stored pressure within the injector body 305 to be released. The pressure release feature 425 may include a hole or a valve with a certain crack pressure. The pressure release feature 425 may permit the plunger to move distally to convey contrast medium 260 from the injector body 305 when the actuation control 320 is activated and to return the plunger 315 proximally when the actuation control 320 is deactivated.

As the plunger 315 is urged proximally, contrast medium 260 from the contrast medium reservoir 400 may be drawn into the injector body 305 to thereby refill the injector body 305 as described above.

Additional configurations may also be provided that include a biasing member 420. For example, the biasing member 420 may include a compression spring placed distal to the plunger 315, an extension spring placed proximal to the plunger 315, or both. Also, the pressure release feature 425 that releases stored pressure within the injector body 305 could be passive, active, automatic, semi-automatic, or manual.

The preceding description has been presented only to illustrate and describe exemplary embodiments. It is not intended to be exhaustive or to limit the disclosure to any precise form disclosed. Many modifications and variations are possible in light of the above teaching. It is intended that the scope of the disclosure be defined by the following claims.

What is claimed is:

1. A system for delivering a contrast medium, comprising:
   a delivery device, including:
      a guidewire lumen and a contrast injection lumen,
         the contrast injection lumen having a proximal end configured to receive a contrast medium and an open distal end configured to deliver a contrast medium to a treatment site within a blood vessel,
         the guidewire lumen and the contrast injection lumen commonly terminating at the distal end and being at least partially conjoined so as to provide axial rigidity to the delivery device; and
   a portable injector device in fluid communication with the contrast injection lumen, the portable injector device including:
      an injector body configured to contain a quantity of the contrast medium;
      a plunger disposed within the injector body;
      a pressure generator including a compressed gas reservoir, and
      a biasing member comprising a spring configured to move the plunger in a proximal direction within the injector body.

2. The system of claim 1, the pressure generator including an actuation control mechanism configured to release pressure from the compressed gas reservoir so as to apply a pressure to the plunger to drive the contrast medium from the injector body and through the open distal end of the contrast injection lumen and into the treatment site within the blood vessel.

3. The system of claim 2, the actuation control mechanism including a pressure regulator.

4. The system of claim 3, the pressure regulator including a pressure release mechanism.

5. The system of claim 1, further comprising a contrast medium reservoir coupled to the portable injector device and the delivery device with a three-passage connection.

6. The system of claim 5, wherein the three-passage connection is configured to allow bi-directional flow between the three-passage connection and the portable injector device, but only allow uni-directional flow between the three-passage connection and the contrast medium reservoir in the direction of the three-passage connection, and only allow uni-directional flow between the three-passage connection and the delivery device in the direction of the delivery device.

\* \* \* \* \*